United States Patent [19]

Origane et al.

[11] Patent Number: 5,188,852
[45] Date of Patent: Feb. 23, 1993

[54] PROCESS FOR PRODUCING YEAST EXTRACT

[75] Inventors: Akira Origane; Takasi Sato, both of Osaka, Japan

[73] Assignee: Oriental Yeast Co., Ltd., Tokyo, Japan

[21] Appl. No.: 602,246

[22] PCT Filed: Feb. 1, 1990

[86] PCT No.: PCT/JP90/00118
  § 371 Date: Oct. 14, 1990
  § 102(e) Date: Oct. 14, 1990

[87] PCT Pub. No.: WO91/11116
  PCT Pub. Date: Aug. 8, 1991

[51] Int. Cl.$^5$ .................................. A23L 1/28
[52] U.S. Cl. ........................... 426/60; 426/61; 426/62; 435/255; 435/256; 435/259
[58] Field of Search ............. 426/60, 61, 62, 7; 435/255, 256, 259

[56] References Cited

U.S. PATENT DOCUMENTS 3,809,780  5/1974  Ishida et al. .................... 426/60
3,881,022  4/1972  Gasser ............................ 426/60
4,285,976  8/1981  Akin et al. ...................... 426/60
5,057,542  10/1991 Leuba et al. .................... 514/844

FOREIGN PATENT DOCUMENTS 57-3345  1/1982  Japan .

OTHER PUBLICATIONS

World Patents Index/Section Ch, Week 7911,/Derwent Publications Ltd., London, GB; Class D, AN 79-21007B/& JP-A-54 017167 (AJINOMOTO) 8 Feb. 1979/*abstract* & JP-B-57 003 345 (. . .).
World Patents Index Latest/Section Ch, Week 8730,/Derwent Publications Ltd., London, GB; Class D, AN 87-210602/& JP-A-62 138 189 (CHOKAN) 20 Jun. 1987/*abstract*.
M. Windholz et al., 'The Merck Index'/1983, Merck & Co., Rahway, N.J. p. 286-287/*2017. chitin*.
World Patents Index/Section Ch, Week 7708,/Derwent Publications Ltd., London, GB; Class B, AN 77-13734Y/& JP-A-52 003 892 (SNOW BRAND MILK) 12 Jan. 1977/*abstract*.
Patent Abstracts of Japan/vol. 14, No. 202 (C-713) 25 Apr. 1990/& JP-A-2 042 953 (ORIENTAL YEAST) 13 Feb. 1990/*abstract*.

Primary Examiner—Joseph Golian
Assistant Examiner—Leslie Wong
Attorney, Agent, or Firm—Browdy and Neimark

[57] ABSTRACT

The present invention relates to a process for producing yeast extract which comprises adding chitosan to yeast thereby to accelerate autolysis. Organic solvents have been added in the past. However, organic solvents are frequently not naturally occurring substances in the concentrations used. When yeast extract is used for food, there are problems with toxicity, flavor, etc. should organic solvents not be completely removed. Accordingly the present invention prepares an excellent yeast extract using chitosan derived from natural substances thereby to accelerate autolysis of yeast without the unwanted problems of organic solvents.

6 Claims, No Drawings

PROCESS FOR PRODUCING YEAST EXTRACT

FIELD OF THE INVENTION

The present invention relates to a process for producing yeast extract and more particularly, to a process for producing yeast extract which can be utilized as food seasonings, nutrient enrichment of food, medium for culturing microorganism, etc.

PRIOR ART

Yeast extract, like meat extract, vegetable extract, fish extract, etc., has a complicated taste and flavor which cannot be attained by chemical seasoning, and has thus been used much as food seasoning. In addition, yeast extract is rich of nutrient components and has also been widely used for nutrient enrichment or as a component for growth media of various microorganisms.

Yeast extract of this kind has been hitherto prepared by autolysis, decomposition with enzyme, chemical decomposition with acids, alkalis, salts, etc. and is characterized by the respective processes.

According to autolysis, enzyme power possessed by yeast bacteria per se is utilized so that the fresher the yeast bacteria, the more difficultly autolysis occurs. Furthermore, the action is slow and its yield is poor but this process is characterized by an excellent taste.

For accelerating the autolysis, organic solvents such as ethyl acetate, toluene, etc. are mainly used. In addition, other methods such as decomposition with enzyme in which enzyme obtained from mold, bacteria or the like is added, addition of saline in a high concentration, etc. have also been adopted.

PROBLEMS TO BE SOLVED BY THE INVENTION

In these prior art processes, however, some substances used to accelerate autolysis are not derived from naturally occurring substances and the resulting products are not sufficiently satisfactory in taste and flavor which are inherently possessed by yeast extract, although the yield is good since the process involves the forced digestion of yeast cells. In addition, yeast extract to which an accelerator for digestion has been added requries steps of evaporation or separation of solvent, desalting of salts, etc. and resultingly requires complicated steps. Moreover, it is also disadvantageous in that depending on additives, utility as food seasoning is restricted. In other words, various processes for preparing yeast extract are hitherto known but when natural matters are wished to be prepared, processes therefor are unsatisfactory since the yield is poor and cost is high. The addition of an accelerator for digestion of yeast encounters a problem that the defects as described above are involved.

MEANS FOR SOLVING THE PROBLEMS

As a result of extensive experiments and investigations to solve the problems described above involved in the prior art processes for preparing yeast extract and to prepare yeast extract having good taste and flavor in good yield, the present inventors have come to accomplish the present invention.

The gist of the present invention lies in adding chitosan to yeast as a raw material in preparing yeast extract. The present invention relates to a process for producing yeast extract characterized by adding 0.01 to 3% by weight of chitosan to live yeast as a raw material.

The present invention also relates to a process for producing yeast extract characterized by adding 0.01 to about 3% by weight of chitosan to live yeast to cause autolysis in the pH range of 2.5 to 7.5 at about 30° to about 54° C. for about 10 to 20 hours.

Chitosan is obtained from shells of crustaceans such as crabs, prawns, krill, etc., insects, fungi, cell walls or the like in which chitosan is present as complexes with calcium or protein. Chitosan has a structure similar to cellulose which is mass-produced by plant. Chitosan is a naturally occurring substance which has been recently used for waste treatment as a high molecular flocculant, as a hair set agent for cosmetics, for medical drug for hemostasis or treating wounds, etc. and as other food materials such as an edible film, a thickener, an emulsion stabilizer, etc.

According to the present invention, the problems in the prior art have been solved by adding chitosan to yeast in preparing yeast extract.

Yeast which is used in the present invention includes not only edible yeasts belonging to the genus Saccharomyces and the genus Pichia but also so-called wild yeasts.

The present invention is characterized by adding chitosan mainly to these yeasts to effect autolysis.

The aforesaid addition amount of chitosan is appropriately controlled depending upon moisture content, viscosity, molecular weight, deacetylation rate, etc. but its addition amount is in the range of 0.01 to 3% based on raw yeast (live yeast). When the amount is less than 0.01%, there is no effect and such is inappropriate. Further even when the amount is larger than 3%, cost simply increases but the effect is not so greater and such is inappropriate. Therefore, the addition amount in the range of 0.05% to 2% is most preferable. The addition within this range provides also the most effective efficiency in cost.

Upon use of chitosan, it is preferred that chitosan be previously dissolved in an acid such as acetic acid, citric acid, tartaric acid, etc.

It is preferred that after adding a chitosan solution to a suspension of live yeast, the mixture be stirred at pH of 2.5 to 7.5 at 30° to 54° C. for 10 to 20 hours or be allowed to stand under these conditions to cause autolysis.

The autolysis solution of yeast is centrifuged, and the resulting supernatant is concentrated as it is, or is dried by spray drying, etc., thereby resulting in paste-like yeast extract or powdery yeast extract.

FUNCTION

Where chitosan is added in the preparation of yeast extract, the mechanism is not exactly known as to how this chitosan acts on yeast as a raw material. However, it has been experimentally confirmed that chitosan acts as an accelerator for autolysis of yeast to give yeast extract in high yield and the process has excellent advantages that upon preparation of yeast extract of the present invention, complicated operational steps such as desalting or distillation, removal of solvent, etc. as in the prior processes are unnecessary.

Next, test examples and examples of the present invention are given.

TEST EXAMPLE 1

In 4 containers, 100 g each of compressed baker's yeast was dispersed in 100 ml of water and a solution of 20 g of chitosan in 20 g of glacial acetic acid was added to the suspension in addition amounts of chitosan of 0.2%, 0.5% and 1.0% in a weight ratio. In extraction time of 0 to 20 hours, pH and yield of yeast extract were examined. A treating temperature was at 45° C. in all the cases.

For control, 2% of toluene was added and the procedures were conducted.

The results are shown in Table 1 below.

TABLE 1

| Extraction hr | Toluene 2% pH | Yield | Chitosan 0.2% pH | Yield | Chitosan 0.5% pH | Yield | Chitosan 1.0% pH | Yield |
|---|---|---|---|---|---|---|---|---|
| 0  | 6.17 | —     | 5.11 | —     | 4.91 | —     | 4.73 | —     |
| 14 | 6.01 | 15.05 | 5.85 | 13.08 | 5.77 | 13.55 | 5.52 | 14.67 |
| 16 | 6.01 | 15.24 | 5.86 | 13.13 | 5.77 | 13.70 | 5.54 | 14.64 |
| 18 | 5.87 | 15.81 | 5.85 | 13.21 | 5.78 | 13.85 | 5.54 | 15.51 |
| 20 | 5.93 | 15.88 | 5.85 | 13.46 | 5.79 | 14.25 | 5.55 | 15.64 |

TEST EXAMPLE 2

Change in pH and yield was examined by varying the treating temperature to 45° C., 50° C. and 55° C. but other conditions being the same as in Test Example 1.

The results are shown in the following Table 2.

TABLE 2

| Temp. | Extraction hr | Toluene 2% pH | Yield | Chitosan 0.2% pH | Yield | Chitosan 0.5% pH | Yield | Chitosan 1.0% pH | Yield |
|---|---|---|---|---|---|---|---|---|---|
| 45° C. | 0  | 5.26 | —    | 5.0  | —    | 4.67 | —    | 4.52 | —    |
|        | 15 | 5.80 | 14.6 | 5.87 | 13.5 | 5.74 | 13.8 | 5.38 | 14.5 |
|        | 20 | 5.81 | 15.8 | 6.01 | 14.7 | 5.74 | 15.2 | 5.4  | 15.7 |
| 50° C. | 0  | 5.62 | —    | 5.16 | —    | 4.86 | —    | 4.60 | —    |
|        | 15 | 5.99 | 14.7 | 5.95 | 12.6 | 5.74 | 13.7 | 5.33 | 15.2 |
|        | 20 | 5.20 | 15.2 | 5.23 | 13.1 | 5.71 | 14.6 | 5.31 | 16.1 |
| 55° C. | 0  | 6.28 | —    | 5.29 | —    | 4.93 | —    | 4.62 | —    |
|        | 15 | 5.58 | 7.8  | 5.97 | 10.9 | 5.72 | 13.6 | 5.32 | 13.5 |
|        | 20 | 5.25 | 8.5  | 5.93 | 11.5 | 5.72 | 13.4 | 5.32 | 14.1 |

TEST EXAMPLE 3

Change in the final pH and yield was examined by varying the amount of acetic acid in the solution of chitosan and acetic acid and varying initial pH but the addition amount of chitosan being the same as 0.2% and other conditions being the same as in Test Example 1.

The results are shown in the following Table 3.

TABLE 3

|  | Toluene 2% | Chitosan 0.2% | Chitosan 0.2% | Chitosan 0.2% | Chitosan 0.2% |
|---|---|---|---|---|---|
| Initial pH | 4.84 | 4.32 | 4.0 | 3.5 | 3.0 |
| Final pH | 6.08 | 6.18 | 5.45 | 4.51 | 4.13 |
| Yield | 15.7 | 13.6 | 14.9 | 16.7 | 15.0 |

EXAMPLE 1

In 1 liter of water was dispersed 1 kg of compressed baker's yeast (300 g of dried yeast) to prepare yeast cream. After 20 g of chitosan (manufactured by Yaizu Fisheries Chemical Co., Ltd.) had been previously dissolved in 20 g of glacial acetic acid, the solution was added to the yeast cream described above while stirring. The pH and temperature of this yeast cream were adjusted to 5.5° and 45° C. and yeast was autolyzed over 18 hours with stirring.

The autolysis solution of this yeast was applied to a centrifuging machine as it was and the supernatant was recovered and spray-dried to give 150 g of yeast extract powder.

The resulting yeast extract powder was used as raw material of powdery soup, whereby soup having good flavor was obtained.

EXAMPLE 2

In 1 liter of water was dispersed 1 kg of compressed brewer's yeast (300 g of dried yeast) to prepare yeast cream. After 15 g of chitosan (manufactured by Shin-Nippon Chemical Co., Ltd.) had been previously dissolved in 20 g of 10% citric acid solution, the resulting solution was added to the yeast cream described above while stirring. The pH and temperature of this yeast cream were adjusted to 5.0° and 45° C. and yeast was autolyzed over 15 hours with stirring.

The autolysis solution of this yeast was applied to a centrifuging machine as it was and the supernatant was recovered and concentrated to give 300 g of yeast extract paste. The paste was excellent as in Example 1 described above.

EFFECTS OF THE INVENTION

The present invention is constructed as described above and exhibits the effects described below.

By adding chitosan in the preparation of yeast extract, chitosan acts as an accelerator for autolysis of yeast so that yeast extract can be obtained in high yield. This chitosan is a naturally occurring substance and requires no post-treatments such as separation or desalting treatments as required in the case of conventional accelerators, and the production steps can thus be simplified. In addition, the fact that chitosan is a naturally occurring substance provides a great advantage that one can eat the obtained yeast extract safely.

We claim:

1. A process for producing yeast extract which comprises;
    adding chitosan to a mixture of live yeast and water to make a ratio of 0.01 to about 3% by weight of chitosan to live yeast;
    allowing the yeast to autolyse in a pH range of 2.5 to 7.5, at about 30° to about 54° C. and for about 10 to about 20 hours to form an autolysate;
    separating solids from the autolysate to obtain a supernatant; and, concentrating or drying the supernatant.

2. The process for producing yeast extract according to claim 1, wherein autolysis of yeast is carried out while stirring.

3. The process for producing yeast extract according to claim 1 wherein the separating is performed by centrifugation.

4. A process for producing yeast extract which comprises;

adding an acid solution of chitosan to a mixture of live yeast and water using a ratio of 0.01 to about 3% by weight of chitosan to live yeast;

allowing the yeast to autolyse in the pH range of 2.5 to 7.5, at about 30° to about 54° C. for about 10 to about 20 hours to form an autolysate;

separating solids from the autolysate to obtain a supernatant; and, concentrating or drying the supernatant.

5. The process for producing yeast extract according to claim 4, wherein autolysis of yeast is carried out while stirring.

6. The process for producing yeast extract according to claim 4 wherein the separating is performed by centrifugation.

* * * * *